(12) United States Patent
Xue et al.

(10) Patent No.: US 8,669,264 B2
(45) Date of Patent: Mar. 11, 2014

(54) RUTAECARPINE DERIVATIVES FOR ACTIVATING CYP1A2 IN A SUBJECT

(75) Inventors: Liang Xue, Elk Grove, CA (US);
William K. Chan, Elk Grove, CA (US);
Stan W. Linnet, Redding, CA (US);
Timothy N. Linnet, Redding, CA (US)

(73) Assignee: Linnet Biopharmaceuticals, Inc., Redding, CA (US)

( * ) Notice: Subject to any disclaimer, the term of this patent is extended or adjusted under 35 U.S.C. 154(b) by 115 days.

(21) Appl. No.: 13/163,658

(22) Filed: Jun. 17, 2011

(65) Prior Publication Data

US 2012/0322816 A1 Dec. 20, 2012

(51) Int. Cl.
*A61K 31/519* (2006.01)
*A61K 31/522* (2006.01)
*C07D 471/12* (2006.01)

(52) U.S. Cl.
USPC .............. 514/263.32; 514/257; 544/245

(58) Field of Classification Search
USPC .............. 514/263.32, 257; 544/245
See application file for complete search history.

(56) References Cited

U.S. PATENT DOCUMENTS

2012/0322812 A1 12/2012 Linnet
2012/0322813 A1 12/2012 Linnet

FOREIGN PATENT DOCUMENTS

WO PCT/US2012/036380 12/2012

OTHER PUBLICATIONS

Don et al., Effect of Structural Modification on the Inhibitory Selectivity of Rutaecarpine Derivatives on Human CYP1A1, CYP1A2, and CYP1B1, 2003, Bioorganic & Medicinal Chemistry Letters, 13, 2535-2538.*
Cazeneuve, et al. Biotransformation of caffeine in human liver microsomes from fetuses, neonates, infants and adults. Br J Clin Pharmac 37:405-412 (1994).
Chen, et al. Caffeine induces cytochrome P4501A2: induction of CYP1A2 by tea in rats. Drug Metab Dispos 24:529-33 (1996).
Evodia, Natural Medicines Comprehensive Database. naturaldatabase.therapeuticresearch.com (downloaded Aug. 15, 2013).
Flockhart. Drug interactions: cytochrome P450 drug interaction table. Indiana University School of Medicine. See http://medicine.iupui.edu/clinpharm/ddis/table.aspx. (2007) (downloaded Jun. 5, 2012).
Gillner, et al. Interactions of rutaecarpine alkaloids with specific binding sites for 2,3,7,8-tetrachlorodibenzo-*p*-dioxin in rat liver. Carcinogenesis 10(4): 651-654 (1989).
Ha, H., et al. Metabolism of theophylline by cDNA-expressed human cytochromes P-450. Br J clin Pharmac: 39: 321-326 (1995).
Hamblin. Insomnia: an ignored health problem. Primary Care: Clinics in Office Practice 34: 649-674 (2007).
Harvey, et al. The subjective meaning of sleep auality: a comparison of individuals with and without insomnia. SLEEP 31(3): (2008).
Jan, et al. Elimination of rutaecarpine and its metabolites in rat feces and urine measured by liquid chromatography. Biomed. Chromatogr. 20: 1163-1171 (2006).
Jia, et al. Pharmacological effects of rutaecarpine as a cardiovascular protective agent. Molecules 15: 1873-1881 (2010).
Jiang, et al. Evodiamine: a novel anti-cancer alkaloid from Evodia rutaecarpa. Molecules 14: 1852-1859 (2009).
Kall, et al. Effects of dietary broccoli on human in vivo drug metabolizing enzymes: evaluation of caffeine, oestrone and chlorzoxazone metabolism. Carcinogenesis 17(4): 793-799 (1996).
Kim, et al. Effect of herbal *Ephedra sinica* and evodia rutaecarpa on body composition and resting metabolic rate: a randomized, double-blind clinical trial in korean premenopausal women. J Acupunct Meridian Stud 1(2): 128-138 (2008).
Lampe, et al. *Brassica* vegetables increase and apiaceous vegetables decrease cytochrome P4501A2 activity in humans: changes in caffeine metabolite ratios in response to controlled vegetable diets. Carcinogenesis 21(6): 1157-1162 (2000).
Lee, et al. Characterization of in vitro metabolites of rutaecarpine in rat liver microsomes using liquid chromatography/tandem mass spectrometry. Rapid Commun. Mass Spectrom. 18: 1073-1080 (2004).
Noh, et al. Effects of rutaecarpine on the metabolism and urinary excretion of caffeine in rats. Arch Pharm Res 34(1): 119-125 (2011).
Ogu, et al. Drug interactions due to cytochrome P450. BUMC Proceedings 13: 421-423 (2000).
Rasmussen, et al. Determination of urinary metabolites of caffeine for the assessment of cytochrome P4501A2, xanthine oxidase, and N-acetyltransferase activity in humans. Ther Drug Monit. (3):254-62 Abstract (Jun. 18, 1996).
Sheu, et al. Antithrombotic effect of rutaecarpine, an alkaloid isolated from evodia rutaecarpa, on platelet plug formation in in vivo experiments. British Journal of Haematology 110: 110-115 (2000).
Siversten, et al. Cognitive behavioral therapy vs. zopiclone for treatment of chronic primary insomnia in older adults: a randomized controlled trial. JAMA 295(24): 2851-2858 (2006).
Steinkellner, et al. Effects of cruciferous vegetables and their constituents on drug metabolizing enzymes involved in the bioactivation of DNA-reactive dietary carcinogens. Mutation Research 480-481: 285-297 (2001).

(Continued)

*Primary Examiner* — Kristin Vajda
(74) *Attorney, Agent, or Firm* — Brian S. Boyer; Syndicated Law PC

(57) ABSTRACT

The teachings provided herein generally relate to compositions comprising rutaecarpine derivatives that activates CYP1A2 through enzyme induction. The uses for such a derivative can include removing caffeine from a subject, improving sleep, treating insomnia, treating caffeine toxicity, treating caffeine addiction and withdrawal symptoms, and the like. Caffeine is just one example of a substrate that can be removed using the derivatives taught herein, and other examples, including theophylline, are provided herein.

20 Claims, 3 Drawing Sheets

(56) References Cited

OTHER PUBLICATIONS

Tang, et al. Assays for CYP1A2 by testing in vivo metabolism of caffeine in humans. Methods in Enzymology 272: 124-130 (1996).
Tariq, et al. Pharmacotherapy for insomnia. Clin. Geriatric Med 24: 93-105 (2008).
Tsai, et al. Effects of evodia rutaecarpa and rutaecarpine on the pharmacokinetics of caffeine in rats. Plant Med 71: 640-645 (2005).
Ueng, et al. Alteration of the pharmacokinetics of theophylline by rutaecarpine, an alkaloid of the medicinal herb Evodia rutaecarpa, in rats. Journal of Pharmacology 57: 227-232 (2005).
Ueng, et al. Induction of cytochrome P450-dependent monooxygenase in mouse liver and kidney by rutaecarpine, an alkaloid of the herbal drug evodia rutaecarpa. Life Sciences 70: 207-217 (2001).
Ueng, et al. Oxidative metabolism of the alkaloid rutaecarpine by human cytochrome P450. Drug Metabolism and Disposition 34: 821-826 (2006).
Ueng, et al. The alkaloid rutaecarpine is a selective inhibitor of cytochrome P450 1A in mouse and human liver microsomes. Drug Metabolism and Disposition 30: 349-353 (2002).
Wilson, et al. Coffee consumption and prostate cancer risk and progression in the health professionals follow-up study. See jnci.oxfordjournals.org (downloaded Apr. 1, 2011).
Xu, et al. Pharmacokinetic comparisions of rutaecarpine and evodiamine after oral administration of Wu-Chu-Yu extracts with different purities to rats. Journal of Ethnopharmacology 139: 395-400 (2012).
Zhao, et al. Quality evaluation of evodia rutaecarpa (Juss.) benth by high performance liquid chromatography with photodiode-array detection. Journal of Pharmaceutical and Biomedical Analysis 48: 1230-1236 (2008).
Zhong, et al. Toxicological assessment on safety of water and 70% ethanolic extracts of nearly ripe fruit of evodia rutaecarpa 33(11): 1317-21 (Jun. 2008).
Zhou, et al. Structure, function, regulation and polymorphism and the clinical significance of human cytochrome P450 1A2. Drug Metabolism Reviews 42(2): 268-354 (2010).
Coffee may reduce risk of lethal prostate cancer in men. http://www.hsph.harvard.edu/news/press-releases/2011-releases/prostate-cancer-coffee-mucci-wilson.html (downloaded Jun. 5, 2012).

\* cited by examiner

RUTAECARPINE DERIVATIVES FOR ACTIVATING CYP1A2 IN A SUBJECT

BACKGROUND

1. Field of the Invention

The teachings provided herein relate to compositions comprising rutaecarpine derivatives that activate CYP1A2 through enzyme induction.

2. Description of Related Art

Caffeine is the world's most widely consumed psychoactive substance, but, unlike many other psychoactive substances, is legal and unregulated in nearly all jurisdictions. Beverages containing caffeine, such as coffee, tea, soft drinks, and energy drinks, enjoy great popularity. In North America, 90% of adults consume caffeine daily.

We spend approx ⅓ of our lives sleeping, and millions of Americans suffer from insomnia. The average adult, for example, should have 8 hours of sleep and usually gets about 6.9 hours of sleep. In 2005, the National sleep foundation survey showed about 75% of all adult Americans reported one or more symptoms of insomnia, and about 33% experienced insomnia almost every night. Caffeine consumption is suggested as significant contributor to the problem.

The problem of insomnia is addressed by several mechanisms in the current market. The mechanisms are generally directed to affecting the level of naturally-occurring neurotransmitters in a subject or stimulating/inhibiting the subject's response to certain neurotransmitters. Benzodiazepine, for example, is considered a first line treatment. Benzodiazepine (BDZ) works on the GABA receptor and improves sleep quality, but it can cause severe side-effects. Non-BDZ drugs promote sleepiness and cause less side-effects, but they can cause amnesia. Both BDZ and non-BDZ drugs carry a dependency risk. Examples include Eszopiclone (LUNESTA), flurazepam (DALMANE), and zolpidem (AMBIEN). Antidepressants are also used, including amitriptyline (ELAVIL), mirtazapine (REMERON), nefazodone (SERZONE), doxepin (ZONALON), and trazodone (DESYREL). Problems with the antidepressants include, but are not limited to, risk of use in the elderly, lack of understanding mode of action, sedation, dizziness, weight gain, and increased risk with cardiovascular disease and high blood pressure. Some over-the-counter medications have also been administered to treat insomnia, such as diphenhydramine. Problems with diphenhydramine include carry-over sedation ("hangover") and tolerance effect. Other over-the-counter drugs that find such use include, but are not limited to, doxylamine, valerian root, and melatonin, where use is limited for at least the reasons of questionable effect and consistency. Other treatments include, for example, non-pharmacological methods of relaxation therapies, behavioral training, sleep hygiene, and stimulus control. Stimulus control (intake control) has been found to be the most effective behavioral intervention.

Pharmacological therapy shows some effectiveness but, as discussed above, several significant problems remain. Behavioral intervention has been shown to be the most effective treatment, but control over stimulant intake, particularly in the form of caffeine remains as a serious, representative compliance problem. About 228 million persons suffer from insomnia at some point throughout the year, and about 101 million persons suffer from insomnia every night. It is reasonably safe to assume that at least 90% of these populations consume caffeine. And, there is no current method of removing caffeine from the system of a subject, that is, caffeine that has already been ingested. As such, the population that has ingested caffeine still suffers an adenosine problem, where their adenosine level does not properly operate as a natural neurotransmitter due to the effect of the caffeine in their system.

Moreover, caffeine toxicity has become a rather serious problem that can result in significant, and possibly fatal, health conditions. Since RED BULL was launched in 1997, for example, energy drinks have become a multibillion dollar industry. More than 500 new products launched in 2006 alone, some of which may be labeled as an "energy supplement." An example 16-ounce can contains two servings, each serving having 130 milligrams of caffeine; 1,000 mg of the organic acid taurine; 200 mg of the compound L-carnitine; 100 mg of inositol; and 50 mg of ginseng extract. The can warns that the drink is powerful and not recommended for children, pregnant women or people who are sensitive to caffeine. These drinks have caused seizures in healthy teenagers with otherwise no history of seizures. It is believed that ingesting too much of these drinks cause side-effects that can range from restlessness and headaches to tremors, confusion and seizures, addiction, and possibly even being fatal, causing irregular heartbeats and severe hypertension or death.

Accordingly, and for at least the above reasons, one of skill will appreciate a method of treating insomnia that carries less risk of side-effects, is more predictable in efficacy and, moreover, can remove caffeine that has already been ingested by the subject. The removal of the caffeine can act as an adenosine treatment, where the removal of caffeine from the system of the subject allows the adenosine to operate normally as a natural neurotransmitter. It should be appreciated that such a treatment can act to improve sleep, treat insomnia, as well as treat caffeine toxicity.

SUMMARY

The teachings provided herein generally relate to compositions comprising a rutaecarpine derivative that activates CYP1A2 through enzyme induction.

The teachings include a compound having the following structure:

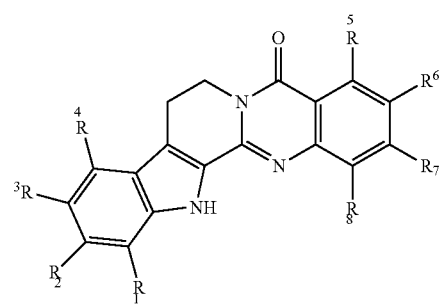

or salts, hydrates or solvates thereof; wherein, at least one of $R_1$-$R_7$ or $R_8$ can be an independently selected electron withdrawing group; and, the remainder of $R_1$-$R_7$ or $R_8$ can comprise a hydrogen, a ($C_1$-$C_4$) alkyl group, or a substituted ($C_1$-$C_4$) alkyl group. A pharmaceutical formulation comprising the compound and a pharmaceutically acceptable excipient are also taught. One of skill will appreciate that the electron withdrawing group can be $NO_2$, a halogen, or an acetyl group.

The teachings also include the following compound:

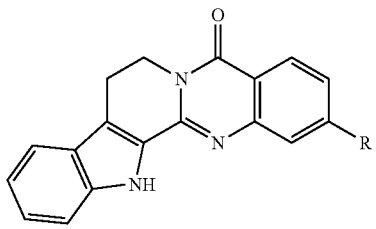

or salts, hydrates or solvates thereof.

R can be NO$_2$, a halogen, or an acetyl group. A pharmaceutical formulation comprising the compound and a pharmaceutically acceptable excipient are also taught. IN some embodiments, R is Cl.

As such, the teachings also include a compound having the structure:

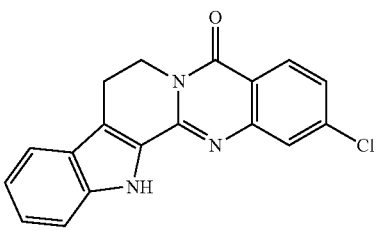 [SMILES: O=c1c2ccc(Cl)cc2nc2n1CCc1c-2[nH]c2ccccc12]

or salts, hydrates or solvates thereof.

The teachings are also directed to an article of manufacture comprising (i) at least one of the compounds and (ii) instructions for administering an effective amount of the compound to a subject.

Methods of using the compounds are also taught. In some embodiments, the teachings are directed to a method of increasing the activity of CYP1A2 in a subject, comprising administering an effective amount of a compound, composition, or formulation taught herein to the subject, wherein the administering increases the activity of CYP1A2 in the subject when compared to a control group that does not receive the compound, composition, or formulation taught herein.

In some embodiments, the teachings are directed to a method of reducing the level of caffeine in a subject, comprising administering an effective amount of a compound, composition, or formulation taught herein to the subject, wherein the administering reducing the level of caffeine in the subject when compared to a control group that does not receive the compound, composition, or formulation taught herein.

In some embodiments, the teachings are directed to a method of improving the quality of sleep in a subject that has consumed caffeine, comprising administering an effective amount of a compound, composition, or formulation taught herein to the subject, wherein the administering improves the quality of sleep in the subject when compared to a control group that does not receive the compound, composition, or formulation taught herein.

In some embodiments, the teachings are directed to a method of treating insomnia in a subject that has consumed caffeine, comprising administering an effective amount of a compound, composition, or formulation taught herein to the subject, wherein the administering reduces the caffeine level in the subject, and improves the amount sleep experienced by the subject, when compared to a control group that does not receive the compound, composition, or formulation taught herein.

In some embodiments, the teachings are directed to a method of treating symptoms of caffeine withdrawal in a subject, comprising administering a combination of (i) an effective amount of a compound, composition, or formulation taught herein and (ii) an analgesic to the subject, wherein the administering reduces the caffeine level in the subject, and ameliorates the symptoms experienced by the subject, when compared to a control group that does not receive the compound, composition, or formulation taught herein. And, in some embodiments, the method includes administering an effective amount of caffeine to the subject.

In some embodiments, the teachings are directed to a method of treating caffeine toxicity in a subject, comprising administering an effective amount of a compound, composition, or formulation taught herein to the subject, wherein the administering reduces the caffeine level in the subject when compared to a control group that does not receive the compound, composition, or formulation taught herein. And, in some embodiments, the method includes administering an effective amount of an analgesic, caffeine, or a combination thereof, to the subject.

In some embodiments, the teachings are directed to a method of treating theophylline toxicity in a subject, comprising administering an effective amount of a compound, composition, or formulation taught herein to the subject, wherein the administering reduces the theophylline level in the subject when compared to a control group that does not receive the compound, composition, or formulation taught herein. And, in some embodiments, the method includes administering an effective amount of theophylline, an analgesic, or a combination thereof, to the subject.

In some embodiments, the teachings are directed to a method of treating a cardiovascular disorder in a subject that has consumed caffeine, comprising administering an effective amount of a compound, composition, or formulation taught herein to the subject, wherein the administering reduces the caffeine level in the subject, and ameliorates symptoms of the cardiovascular disorder in the subject, when compared to a control group that does not receive the compound, composition, or formulation taught herein.

One of skill reading the teachings that follow will appreciate that the concepts can extend into additional embodiments that go well-beyond a literal reading of the claims, the inventions recited by the claims, and the terms recited in the claims.

DETAILED DESCRIPTION

Figure 1:
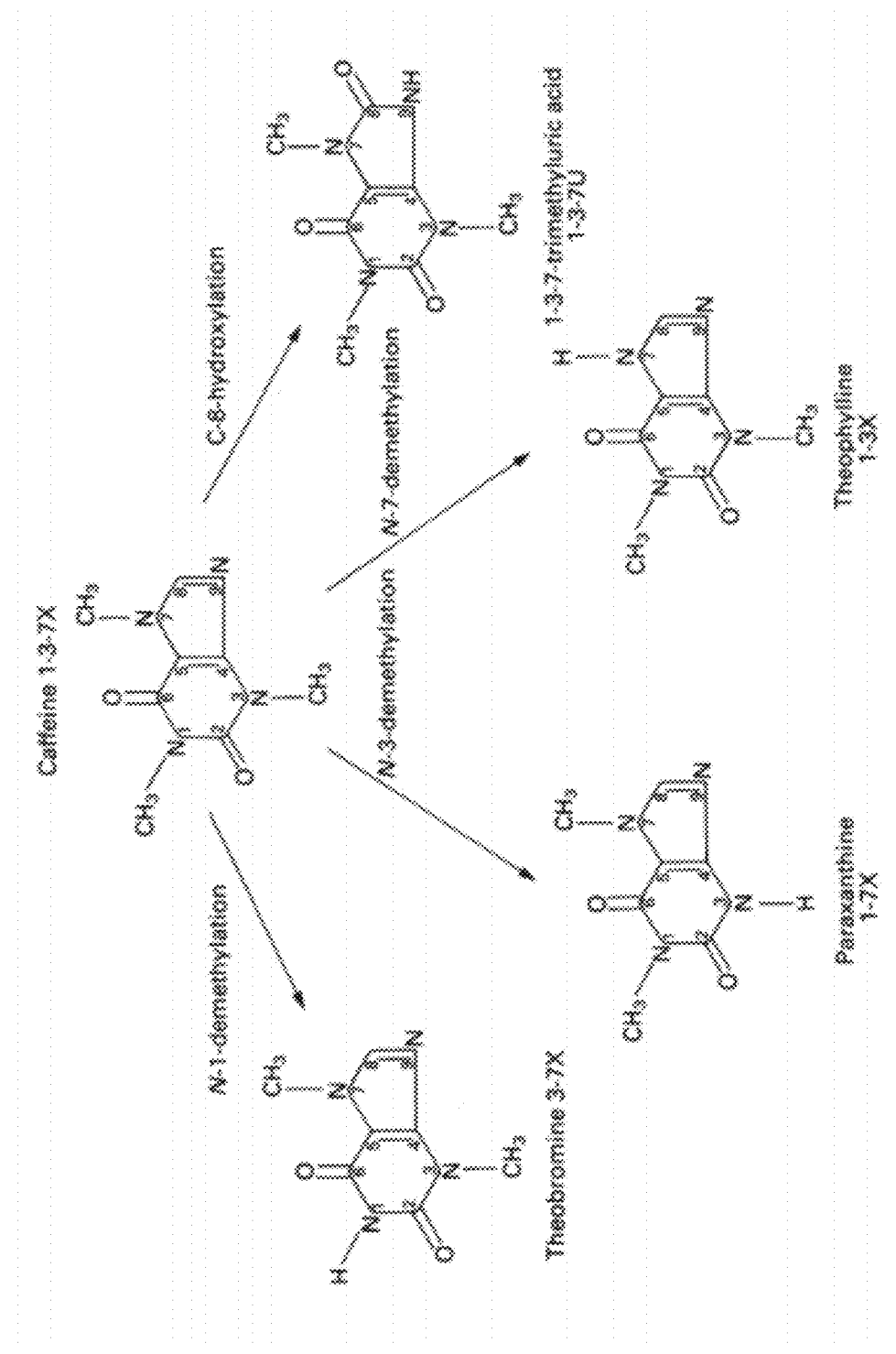
FIG. 1 illustrates how caffeine is primarily metabolized to paraxanthine via CYP1A2 enzyme in a human, according to some embodiments.

The teachings provided herein generally relate to compositions comprising a rutaecarpine derivative that activates CYP1A2 through enzyme induction. More particularly, compounds, compositions, or formulations comprising a rutaecarpine derivative for use in treating caffeine-related conditions that include for example, reduced sleep quality, insomnia, caffeine toxicity, caffeine addiction, withdrawal symptoms, and the like.

The teachings include a compound having the following structure:

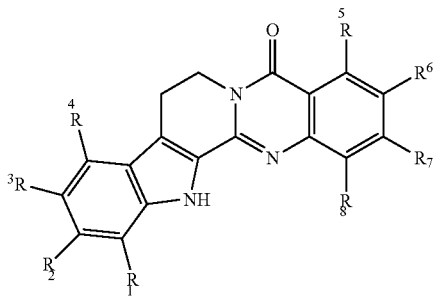

or salts, hydrates or solvates thereof.

At least one of $R_1$-$R_7$ or $R_8$ can be an independently selected electron withdrawing group; and, the remainder of $R_1$-$R_7$ or $R_8$ can comprise a hydrogen, a ($C_1$-$C_4$) alkyl group, or a substituted ($C_1$-$C_4$) alkyl group. A pharmaceutical formulation comprising the compound and a pharmaceutically acceptable excipient are also taught. One of skill will appreciate that the electron withdrawing group can be $NO_2$, a halogen, or an acetyl group.

The teachings also include the following compound:

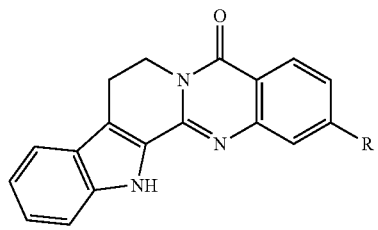

or salts, hydrates or solvates thereof.

R can be $NO_2$, a halogen, or an acetyl group. A pharmaceutical formulation comprising the compound and a pharmaceutically acceptable excipient are also taught. IN some embodiments, R is Cl.

As such, the teachings also include a compound having the structure:

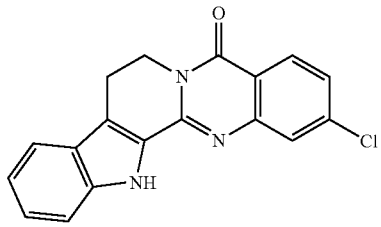 [SMILES: O=c1c2ccc(Cl)cc2nc2n1CCc1c-2[nH]c2ccccc12]

or salts, hydrates or solvates thereof.

The teachings are also directed to an article of manufacture comprising (i) at least one of the compounds and (ii) instructions for administering an effective amount of the compound to a subject.

The R groups can be any functional group that one of skill would or could substitute and still obtain the functions consistent with the teachings provided herein. For example, in some embodiments, an R group can be an alkyl, alkanyl, alkenyl, alkynyl, alkoxy, acyl, aryl, aralkyl, halo, heteroalkyl, heteroalkanyl, heteroalkenyl, heteroalkynyl, heteroaryl, heteroaralkyl, and the like.

"Alkyl," by itself or as part of another substituent, can refer to a saturated or unsaturated, branched, straight-chain or cyclic monovalent hydrocarbon radical derived by the removal of one hydrogen atom from a single carbon atom of a parent alkane, alkene or alkyne. Typical alkyl groups can include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In some embodiments, an alkyl group comprises from 1 to 2, 1 to 3, 1 to 4, 1 to 5, 1 to 6, 1 to 7, 1 to 8, 1 to 9, or 1 to 10 carbon atoms ($C_1$-$C_{10}$ alkyl). In some embodiments, an alkyl group comprises from about 1 to 3 to about 1 to 6 carbon atoms (from $C_1$-$C_3$ to $C_1$-$C_6$ alkyl). In some embodiments, an alkyl group comprises from 1 to 4 carbon atoms ($C_1$-$C_4$ alkyl).

"Alkanyl," by itself or as part of another substituent, can refer to a saturated branched, straight-chain or cyclic alkyl radical derived by the removal of one hydrogen atom from a single carbon atom of a parent alkane. Typical alkanyl groups can include, but are not limited to, methanyl; ethanyl; propanyls such as propan-1-yl, propan-2-yl(isopropyl), cyclopropan-1-yl, etc.; butanyls such as butan-1-yl, butan-2-yl(sec-butyl), 2-methyl-propan-1-yl(isobutyl), 2-methyl-propan-2-yl(t-butyl), cyclobutan-1-yl, etc.; and the like.

"Alkenyl," by itself or as part of another substituent, can refer to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups can include, but are not limited to, ethenyl; propenyls such as prop-1-en-1-yl, prop-1-en-2-yl, prop-2-en-1-yl(allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent can refer to an unsaturated branched, straight-chain or cyclic alkyl radical having at least one carbon-carbon triple bond derived by the removal of one hydrogen atom from a single carbon atom of a parent alkyne. Typical alkynyl groups can include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkoxy," by itself or as part of another substituent, can refer to a radical of the formula —O—$R^{400}$, where $R^{400}$ is alkyl or substituted alkyl as defined herein.

"Acyl" by itself or as part of another substituent can refer to a radical —C(O)$R^{401}$, where $R^{401}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, can refer to a monovalent aromatic hydrocarbon group derived by the removal of one hydrogen atom from a single carbon atom of a parent aromatic ring system, as defined herein. Typical aryl groups can include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In some embodiments, an aryl group comprises from 6 to 15 carbon atoms ($C_6$-$C_{15}$ aryl). In still other embodiments, an aryl group comprises from 6 to 15 carbon atoms ($C_6$-$C_{10}$ aryl).

"Arylalkyl," by itself or as part of another substituent, can refer to an acyclic alkyl group in which one of the hydrogen atoms bonded to a carbon atom, typically a terminal or $sp^3$ carbon atom, is replaced with an aryl group as, as defined herein. Typical arylalkyl groups can include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In some embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Compounds" can refer to compounds encompassed by structural formulae disclosed herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds of the invention include, but are not limited to, $^2$H, $^3$H, $^{13}$C, $^{14}$C, $^{15}$N, $^{18}$O, $^{17}$O, etc. Compounds may exist in unsolvated or unhydrated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule.

An "electron withdrawing group" can refer to a chemical functional group that draws electrons away from a reaction center. Examples of electron withdrawing groups can include halogens (e.g., Cl,). nitriles (e.g., CN); carbonyls (e.g., CO), and nitro groups ($NO_2$). Any one or any combination of nitro, acyl, formyl, alkylsulfonyl, arylsulfonyl, trifluoromethyl, cyano, halo (e.g., fluoro, chloro, bromo, and iodo) moieties, and other electron-withdrawing groups can be used in some embodiments. In some embodiments, halo, nitrate and fluoromethyl groups ($CF_3$, $CHF_2$ or $CH_2F$) can be suitable electron withdrawing groups. One of skill will appreciate that there are several atoms, chemical groups, or structures, i.e., chemical moieties, that can function as an electron withdrawing group for purposes of the teachings provided herein. Whether a particular chemical moiety acts as an electron withdrawing group can depend on the nature of the neighboring chemical moiety or moieties, as an electron withdrawing group draws electron density from neighboring atoms towards itself, usually by resonance or inductive effects. In some embodiments, a weaker base can draw electrons from stronger base. For purposes of illustration, trifluoroacetate ion is a weaker base than acetate ion because the trifluoromethyl group is able to draw electron density away from the carboxylate when in a neighboring chemical relationship, making the trifluoromethyl group an electron withdrawing group in this situation. One of skill will appreciate that electron withdrawing groups can be added in one or more positions of a chemical structure to produce a cumulative effect, and each electron withdrawing group can be independently selected.

"Halogen", or "halo," by itself or as part of another substituent can refer to a radical —F, —Cl, —Br or —I.

"Heteroalkyl," "Heteroalkanyl," "Heteroalkenyl" and "Heteroalkynyl," by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups can include, but are not limited to, —O—, —S—, —O—O—, —S—S—, —O—S—, —NR$^{501}$R$^{502}$—, =N—N=, —N=N—, —N=N—NR$^{503}$R$^{404}$, —PR$^{505}$—, —P(O)$_2$—, —POR$^{506}$—, —O—P(O)$_2$—, —SO—, —SO$_2$—, —SnR$^{507}$R$^{508}$— and the like, where R$^{501}$, R$^{502}$, R$^{503}$, R$^{504}$, R$^{505}$, R$^{506}$, R$^{507}$ and R$^{508}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl," by itself or as part of another substituent, can refer to a monovalent heteroaromatic radical derived by the removal of one hydrogen atom from a single atom of a parent heteroaromatic ring systems, as defined herein. Typical heteroaryl groups can include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In some embodiments, the heteroaryl group comprises from 5 to 10 ring atoms (5-10 membered heteroaryl). Exemplary heteroaryl groups can include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent can refer to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is (C$_1$-C$_6$) alkyl and the heteroaryl moiety is a 5-15-membered heteroaryl. In some embodiments, the heteroarylalkyl is a 6-13 membered heteroarylalkyl, e.g., the alkanyl, alkenyl or alkynyl moiety is (C$_1$-C$_3$) alkyl and the heteroaryl moiety is a 5-10 membered heteroaryl.

"Parent Aromatic Ring System" can refer to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" can refer to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Protecting group" can refer to a grouping of atoms that when attached to a reactive functional group in a molecule masks, reduces or prevents reactivity of the functional group during chemical synthesis. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1-8 (John Wiley and Sons, 1971-1996). Representative amino protecting groups can include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups can include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" can refer to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —OS$(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC$(S)$OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups can include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —OS$(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists that are useful for substituting other specified groups or atoms will be apparent to those of skill in the art. The substituents used to substitute a specified group can be further substituted, typically with one or more of the same or different groups selected from the various groups specified above.

There are several methods of use of the compounds, compositions, and formulations provided herein. In some embodiments, the teachings are directed to a method of increasing the activity of CYP1A2 in a subject, comprising administering an effective amount of a compound, composition, or formulation taught herein to the subject, wherein the administering increases the activity of CYP1A2 in the subject when compared to a control group that does not receive the compound, composition, or formulation taught herein.

It should be appreciated that CYP1A2 can act on a variety of substrates, including, but not limited to caffeine, theophylline, and phenacetin. The activity of the enzyme can serve to remove each of the substrates from the system of a subject. Moreover, it should be appreciated that the compounds, compositions, and formulations taught herein can be referred to, in some embodiments, as inducers of CYP1A2. Other inducers may include brassica vegetables, such as broccoli, cabbage, and brussel sprouts, for example. Without intending to be bound by any mechanism or theory of action, the AhR transduction pathway is assumed to be the induction pathway for inducing the CYP1A2 through administration of the compounds, compositions, and formulations taught herein. One of skill will appreciate the number of applications of the teachings herein, such as removal of a substrate, treatment of dependency on a substrate and withdrawal, as well as treatment for toxicity problem due to too much of a substrate being in the system of a subject. Moreover, there are a number of related disorders that can be treated using the teachings provided herein to remove a particular substrate. To test a contemplated method, one of skill can use generally accepted laboratory techniques. For example, the compounds, compositions, and formulations taught herein can be administered to a rat for a desired amount of time, such as 2-3 days pretreatment. Subsequently, perhaps day 4, a substrate can be administered to the rat, and the substrate concentrate in the rat can be measured. Data can be obtained, for example, using standard non-compartmental models and pharmacokinetic studies to determine the reduction in substrate level in the rat. For in vitro studies, one of skill will appreciate that phenacetin, 7-ethoxycoumarin, and ethoxyresorufin can each be used, for example, as a probe for determining CYP1 A2 activity.

In some embodiments, CYP1A2 substrates include, but are not limited to, caffeine, phenacetin, theophylline, tacrine, tizanidine, 7-methoxyresorufin, 7-ethoxyresorufin, 7-ethoxycoumarin, melatonin, hexachloroethane, and MelQ. And, in some embodiments, CYP1A2 substrates include, but are not limited to, R-acenocoumarol, acetaminophen, albendazole, almotriptan, alosetron, amiodarone, aminoflavone, aminopyrine, amitriptyline, antipyrine, azelastine, banzydamine, $O^6$-benzylguanine, bortezomib, bufuralol, bupivacaine, caffeine, carbamazepine, carvedilol, chlorzoxazone, cilostazol, cinnarizine, cisapride, cloimpramine, clozapine, coumarin, cyclobenzaprine, dacarbazine, desipramine, 5,6-dimethylxanthenone-4 acetic acid, dephenhydramine, disopyramide, DMXB, doxepin, duloxetine, efavirenz, erlotinib, estradiol, flunarizine, flunitrazepam, flutamide, fluoxetine, fluvoxamine, furafylline, guanabenz, haloperidol, iloperidone, imatinib, indiplon, imipramine, imiquimod, KR-62980, KR-63198, leflunomide, levobupivacaine, lidocaine, lisofylline, lu 25-109, maprotiline, melatonin, S-mephenytoin, metoclopramide, mexiletine, mianserin, mirtazapine, naproxen, nabumetone, nicardipine, nicotine, nordiazepam, nortriptyline, olanzapine, ondansetron, paraxanthine, pentoxifylline, perphenazine, pefloxacin, phenacetin, pimobendan, pimozide, pioglitazone, primaquine, pranidipine, proguanil, promazine, propafenone, propofol, propranolol, ranitidine, resiquimod, riluzole, rofecoxib, ropinirole, ropivacaine, selegiline, sertraline, tacrine, tegafur, terbinafine, thalidomide, theophylline, thiobendazole, thioridazine, tizanidine, trazodone, triamterene, verpamil, r-warfarin, WHI-P131, YM992, zileuton, zolmitriptan, zolpidem, zotepine, and zoxazolamine.

As such, in some embodiments, the teachings are directed to a method of reducing the level of caffeine in a subject, comprising administering an effective amount of a compound, composition, or formulation taught herein to the subject, wherein the administering reducing the level of caffeine in the subject when compared to a control group that does not receive the compound, composition, or formulation taught herein.

Reducing the level of caffeine can result in a variety of treatments in a subject. In some embodiments, the teachings are directed to a method of improving the quality of sleep in a subject that has consumed caffeine, comprising administering an effective amount of a compound, composition, or formulation taught herein to the subject, wherein the administering improves the quality of sleep in the subject when compared to a control group that does not receive the compound, composition, or formulation taught herein.

Likewise, in some embodiments, the teachings are directed to a method of treating insomnia in a subject that has consumed caffeine, comprising administering an effective amount of a compound, composition, or formulation taught herein to the subject, wherein the administering reduces the caffeine level in the subject, and improves the amount sleep experienced by the subject, when compared to a control group that does not receive the compound, composition, or formulation taught herein.

Likewise, in some embodiments, the teachings are directed to a method of treating symptoms of caffeine withdrawal in a subject, comprising administering a combination of (i) an effective amount of a compound, composition, or formulation taught herein and (ii) an analgesic to the subject, wherein the administering reduces the caffeine level in the subject, and ameliorates the symptoms experienced by the subject, when compared to a control group that does not receive the compound, composition, or formulation taught herein. And, in some embodiments, the method includes administering an effective amount of caffeine to the subject.

Likewise, in some embodiments, the teachings are directed to a method of treating caffeine toxicity in a subject, comprising administering an effective amount of a compound, composition, or formulation taught herein to the subject, wherein the administering reduces the caffeine level in the subject when compared to a control group that does not receive the compound, composition, or formulation taught herein. And, in some embodiments, the method includes administering an effective amount of an analgesic, caffeine, or a combination thereof, to the subject.

In some embodiments, the teachings are directed to a method of treating theophylline toxicity in a subject, comprising administering an effective amount of a compound, composition, or formulation taught herein to the subject, wherein the administering reduces the theophylline level in the subject when compared to a control group that does not receive the compound, composition, or formulation taught herein. And, in some embodiments, the method includes administering an effective amount of theophylline, an analgesic, or a combination thereof, to the subject.

The use of theophylline is complicated by its interaction with various drugs, chiefly cimetidine and phenytoin, and that it has a narrow therapeutic index, so its use must be monitored to avoid toxicity. It can also cause nausea, diarrhea, increase in heart rate, arrhythmias, and CNS excitation (headaches, insomnia, irritability, dizziness and lightheadedness). Seizures can also occur in severe cases of toxicity and is considered to be a neurological emergency. Its toxicity is increased by erythromycin, cimetidine, and fluoroquinolones, such as ciprofloxacin. It can reach toxic levels when taken with fatty meals, an effect called dose dumping.

In some embodiments, the teachings are directed to a method of treating a cardiovascular disorder in a subject that has consumed caffeine, comprising administering an effective amount of a compound, composition, or formulation taught herein to the subject, wherein the administering reduces the caffeine level in the subject, and ameliorates symptoms of the cardiovascular disorder in the subject, when compared to a control group that does not receive the compound, composition, or formulation taught herein.

In some embodiments, the methods taught herein can further include the administration of an effective amount of an additional bioactive agent or therapeutic treatment. In some embodiments, the terms "agent" and "therapy" can be interchangeable. In many embodiments, the molecular weight of an agent should be at or below about 40,000 Daltons to ensure elimination of the agent from a subject. In some embodiments, the molecular weight of the agent ranges from about 300 Daltons to about 40,000 Daltons, from about 8,000 Daltons to about 30,000 Daltons, from about 10,000 Daltons to about 20,000 Daltons, or any range therein.

A bioactive agent can be any moiety capable of contributing to a therapeutic effect, a prophylactic effect, both a therapeutic and prophylactic effect, or other biologically active effect in a subject. A bioactive agent can also have diagnostic properties. The bioactive agents include, but are not limited to, small molecules, nucleotides, oligonucleotides, polynucleotides, amino acids, oligopeptides, polypeptides, and proteins.

It should be appreciated that, a bioactive agent can be given alone or in combination with other bioactive agents, with the compositions and methods taught herein. The agent can be caffeine, an analgesic, or a combination thereof, in some embodiments. Examples of analgesics include peracetamol, NSAID's, and COX-2 inhibitors. When drugs having different effects are combined, each drug can be used at its optimal dose, sometimes without, and sometimes reducing, intolerable side-effects.

Methods of Administration

The compositions can provide a therapeutic and/or prophylactic effect in the treatment of a disease, or ameliorization of one or more symptoms of a disease in a subject. The term "subject" and "patient" are used interchangeably and refer to an animal such as a mammal including, but not limited to, non-primates such as, for example, a cow, pig, horse, cat, dog, rat and mouse; and primates such as, for example, a monkey or a human.

The compositions provided herein can be administered to a subject using any manner of administration known to one of skill. For example, in some embodiments, a localized administration is used and, in some embodiments a systemic administration is used. In some embodiments, a combination of system and local administration is used. One of skill will appreciate that the therapeutic program selected, the agents administered, the condition of the subject, and the effects desired, can affect the administration schedule and program used.

One of skill understands that the amount of the agents administered can vary according to factors such as, for example, the type of disease, age, sex, and weight of the subject, as well as the method of administration. For example, local and systemic administration can call for substantially different amounts to be effective. Dosage regimens may also be adjusted to optimize a therapeutic response. In some embodiments, a single bolus may be administered; several divided doses may be administered over time; the dose may be proportionally reduced or increased; or, any combination thereof, as indicated by the exigencies of the therapeutic situation and factors known one of skill in the art. It is to be noted that dosage values may vary with the severity of the condition to be alleviated. Dosage regimens may be adjusted over time according to the individual need and the professional judgment of the person administering or supervising the administration of the compositions, and the dosage ranges set forth herein are exemplary only and do not limit the dosage ranges that may be selected by medical practitioners.

The terms "administration" or "administering" refer to a method of incorporating a composition into the cells or tissues of a subject, either in vivo or ex vivo to diagnose, prevent, treat, or ameliorate a symptom of a disease. In one example, a compound can be administered to a subject in vivo parenterally. In another example, a compound can be administered to a subject by combining the compound with cell tissue from the subject ex vivo for purposes that include, but are not limited to, assays for determining utility and efficacy of a composition. When the compound is incorporated in the subject in combination with one or active agents, the terms "administration" or "administering" can include sequential or concurrent incorporation of the compound with the other agents such as, for example, any agent described above. A pharmaceutical composition of the invention is formulated to be compatible with its intended route of administration. Examples of routes of administration include, but are not limited to, parenteral such as, for example, intravenous, intradermal, intramuscular, and subcutaneous injection; oral; inhalation; intranasal; transdermal; transmucosal; and rectal administration.

An "effective amount" of a compound of the invention can be used to describe a therapeutically effective amount or a prophylactically effective amount. An effective amount can also be an amount that ameliorates the symptoms of a disease. A "therapeutically effective amount" can refer to an amount that is effective at the dosages and periods of time necessary to achieve a desired therapeutic result and may also refer to an amount of active compound, prodrug or pharmaceutical agent that elicits any biological or medicinal response in a tissue, system, or subject that is sought by a researcher, veterinarian, medical doctor or other clinician that may be part of a treatment plan leading to a desired effect. In some embodiments, the therapeutically effective amount may need to be administered in an amount sufficient to result in amelioration of one or more symptoms of a disorder, prevention of the advancement of a disorder, or regression of a disorder. In some embodiments, for example, a therapeutically effective amount can refer to the amount of an agent that provides a measurable response of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of a desired action of the composition. The term "treating" can refer to the administering one or more therapeutic or prophylactic agents taught herein.

A "prophylactically effective amount" can refer to an amount that is effective at the dosages and periods of time necessary to achieve a desired prophylactic result such as, preventing, inhibiting, or reversing angiogenesis, tumor growth, or tumor invasion. Typically, a prophylactic dose is used in a subject prior to the onset of a disease, or at an early stage of the onset of a disease, to prevent or inhibit onset of the disease or symptoms of the disease. A prophylactically effective amount may be less than, greater than, or equal to a therapeutically effective amount.

The administration can be local or systemic. In some embodiments, the administration can be oral. In some embodiments, the administration can be subcutaneous injection. In some embodiments, the administration can be intravenous injection using a sterile isotonic aqueous buffer. In another embodiment, the administration can include a solubilizing agent and a local anesthetic such as lignocaine to ease discomfort at the site of injection. In some embodiments, the administrations may be parenteral to obtain, for example, ease and uniformity of administration.

Any administration vehicle known to one of skill to be suitable for administration of the compounds, compositions, and formulations taught herein can be used. A "vehicle" can refer to, for example, a diluent, excipient or carrier with which a compound is administered to a subject.

The compounds can be administered in dosage units. The term "dosage unit" can refer to discrete, predetermined quantities of a compound that can be administered as unitary dosages to a subject. A predetermined quantity of active compound can be selected to produce a desired therapeutic effect and can be administered with a pharmaceutically acceptable carrier. The predetermined quantity in each unit dosage can depend on factors that include, but are not limited to, (a) the unique characteristics of the active compound and the particular therapeutic effect to be achieved, and (b) the limitations inherent in the art of creating and administering such dosage units.

A "pharmaceutically acceptable carrier" is a diluent, adjuvant, excipient, or vehicle with which the composition is administered. A carrier is pharmaceutically acceptable after approval by a state or federal regulatory agency or listing in the U.S. Pharmacopeial Convention or other generally recognized sources for use in subjects.

The pharmaceutical carriers include any and all physiologically compatible solvents, dispersion media, coatings, antibacterial and antifungal agents, isotonic and absorption delaying agents, and the like. Examples of pharmaceutical carriers include, but are not limited to, sterile liquids, such as water, oils and lipids such as, for example, phospholipids and glycolipids. These sterile liquids include, but are not limited to, those derived from petroleum, animal, vegetable or synthetic origin such as, for example, peanut oil, soybean oil, mineral oil, sesame oil, and the like. Water can be a preferred carrier for intravenous administration. Saline solutions, aqueous dextrose and glycerol solutions can also be liquid carriers, particularly for injectable solutions.

Suitable pharmaceutical excipients include, but are not limited to, starch, sugars, inert polymers, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain minor amounts of wetting agents, emulsifying agents, pH buffering agents, or a combination thereof. The compositions can take the form of solutions, suspensions, emulsion, tablets, pills, capsules, powders, sustained-release formulations and the like. Oral formulations can include standard carriers such as, for example, pharmaceutical grades mannitol, lactose, starch, magnesium stearate, sodium saccharine, cellulose, magnesium carbonate, and the like. See Martin, E. W. Remington's Pharmaceutical Sciences. Supplementary active compounds can also be incorporated into the compositions.

In some embodiments, the carrier is suitable for parenteral administration. In some embodiments, the carrier can be suitable for intravenous, intraperitoneal, intramuscular, sublingual or oral administration. In some embodiments, the pharmaceutically acceptable carrier may comprise pharmaceutically acceptable salts.

Pharmaceutical formulations for parenteral administration may include liposomes. Liposomes and emulsions are delivery vehicles or carriers that are especially useful for hydrophobic drugs. Depending on biological stability of the therapeutic reagent, additional strategies for protein stabilization may be employed. Furthermore, one may administer the drug in a targeted drug delivery system such as, for example, in a liposome coated with target-specific antibody. The liposomes can be designed, for example, to bind to a target protein and be taken up selectively by the cell expressing the target protein.

Therapeutic compositions typically must be sterile and stable under the conditions of manufacture and storage. The composition can be formulated as a solution, microemulsion, liposome, or other ordered structure suitable for a high drug concentration. In some embodiments, the carrier can be a solvent or dispersion medium including, but not limited to, water; ethanol; a polyol such as for example, glycerol, propylene glycol, liquid polyethylene glycol, and the like; and, combinations thereof. The proper fluidity can be maintained in a variety of ways such as, for example, using a coating such as lecithin, maintaining a required particle size in dispersions, and using surfactants.

In some embodiments, isotonic agents can be used such as, for example, sugars; polyalcohols that include, but are not limited to, mannitol, sorbitol, glycerol, and combinations thereof; and sodium chloride. Sustained absorption characteristics can be introduced into the compositions by including agents that delay absorption such as, for example, monostearate salts, gelatin, and slow release polymers. Carriers can be used to protect active compounds against rapid release, and such carriers include, but are not limited to, controlled release formulations in implants and microencapsulated delivery systems. Biodegradable and biocompatible polymers can be used such as, for example, ethylene vinyl acetate, polyanhydrides, polyglycolic acid, collagen, polyorthoesters, polylactic acid, polycaprolactone, polyglycolic copolymer (PLG), and the like. Such formulations can generally be prepared using methods known to one of skill in the art.

The compounds may be administered as suspensions such as, for example, oily suspensions for injection. Lipophilic solvents or vehicles include, but are not limited to, fatty oils such as, for example, sesame oil; synthetic fatty acid esters, such as ethyl oleate or triglycerides; and liposomes. Suspensions that can be used for injection may also contain substances that increase the viscosity of the suspension such as, for example, sodium carboxymethyl cellulose, sorbitol, or dextran. Optionally, a suspension may contain stabilizers or agents that increase the solubility of the compounds and allow for preparation of highly concentrated solutions.

In one embodiment, a sterile and injectable solution can be prepared by incorporating an effective amount of an active compound in a solvent with any one or any combination of desired additional ingredients described above, filtering, and then sterilizing the solution. In another embodiment, dispersions can be prepared by incorporating an active compound into a sterile vehicle containing a dispersion medium and any one or any combination of desired additional ingredients described above. Sterile powders can be prepared for use in sterile and injectable solutions by vacuum drying, freeze-drying, or a combination thereof, to yield a powder that can be comprised of the active ingredient and any desired additional ingredients. Moreover, the additional ingredients can be from a separately prepared sterile and filtered solution. In another embodiment, the active agent may be prepared in combination with one or more additional compounds that enhance the solubility of the active agent.

In some embodiments, a therapeutically or prophylactically effective amount of a composition may range in concentration from about 0.001 nM to about 0.10 M; from about 0.001 nM to about 0.5 M; from about 0.01 nM to about 150 nM; from about 0.01 nM to about 500 µM; from about 0.01 nM to about 1000 nM, 0.001 µM to about 0.10 M; from about 0.001 µM to about 0.5 M; from about 0.01 µM to about 150 µM; from about 0.01 µM to about 500 µM; from about 0.01 µM to about 1000 nM, or any range therein. In some embodiments, the compositions may be administered in an amount ranging from about 0.001 mg/kg to about 500 mg/kg; from about 0.005 mg/kg to about 400 mg/kg; from about 0.01 mg/kg to about 300 mg/kg; from about 0.01 mg/kg to about 250 mg/kg; from about 0.1 mg/kg to about 200 mg/kg; from about 0.2 mg/kg to about 150 mg/kg; from about 0.4 mg/kg to about 120 mg/kg; from about 0.15 mg/kg to about 100 mg/kg, from about 0.15 mg/kg to about 50 mg/kg, from about 0.5 mg/kg to about 10 mg/kg, or any range therein, wherein a human subject is often assumed to average about 70 kg.

In some embodiments, the compounds can be administered by inhalation through an aerosol spray or a nebulizer that may include a suitable propellant such as, for example, dichlorodifluoromethane, trichlorofluoromethane, dichlorotetrafluoroethane, carbon dioxide, or a combination thereof. In one example, a dosage unit for a pressurized aerosol may be delivered through a metering valve. In another embodiment, capsules and cartridges of gelatin, for example, may be used in an inhaler and can be formulated to contain a powderized mix of the compound with a suitable powder base such as, for example, starch or lactose.

The present invention encompasses sustained release formulations for the administration of one or more agents. In some embodiments, the sustained release formulations can reduce the dosage and/or frequency of the administrations of such agents to a subject.

The compositions can be administered as a pharmaceutical formulation by injection. In some embodiments, the formulation can comprise the extract in combination with an aqueous injectable excipient. Examples of suitable aqueous injectable excipients are well known to persons of ordinary skill in the art, and they, and the methods of formulating the formulations, may be found in such standard references as Alfonso A R: Remington's Pharmaceutical Sciences, 17th ed., Mack Publishing Company, Easton Pa., 1985. Suitable aqueous injectable excipients include water, aqueous saline solution, aqueous dextrose solution, and the like, optionally containing dissolution enhancers for the acid-modified arabinogalactan protein composition, such as solution of mannitol or other sugars, or a solution of glycine or other amino acids.

Typically, a composition taught herein can be administered by subcutaneously, intramuscularly, intraperitoneally, or intravenously, injecting. A localized administration can, in some embodiments, include direct injection of an agent into the region of the tissue to be treated such as, for example, a solid tumor. In some embodiments, intravenous administration is used, and it can be continuous intravenous infusion over a period of a few minutes to an hour or more, such as around fifteen minutes. The amount administered may vary widely depending on the type of formulation, size of a unit dosage, kind of excipients, and other factors well known to those of ordinary skill in the art. The formulation may comprise, for example, from about 0.0001% to about 10% (w/w), from about 0.01% to about 1%, from about 0.1% to about 0.8%, or any range therein, with the remainder comprising the excipient or excipients.

In some embodiments, the composition can be administered in conjunction with at least one other therapeutic agent for the disease state being treated, especially another agent capable of alleviating the symptoms of toxicity associated with caffeine or theophylline such as, for example, caffeine, theophylline, or an analgesic. The amounts of the agents needed can be reduced, even substantially, such that the amount of the agent or agents required is reduced to the extent that a significant response is observed from the subject. A significant response can include, but is not limited to, a reduction or elimination of nausea, a visible increase in tolerance, a faster response to the treatment, a more selective response to the treatment, or a combination thereof.

In some embodiments, an effective amount can range, for example, from about 1 mg/day to about 1000 mg/day, from about 10 mg/day to about 500 mg/day, from about 50 mg/day to about 250 mg/day, or any range therein, for a human of average body mass (e.g., 75 kg, in some embodiments). A person of ordinary skill in the art will be able without undue experimentation, having regard to that skill and this disclosure, to determine a therapeutically effective amount of the compositions of this invention for a given disease.

In some embodiments, the compounds, compositions, and formulations can be administered in combination with a composition taught herein using any amount, time, and method of administration known to be effective by one of skill. The compound can be administered, for example, in an amount ranging from about 0.1 µg/kg to about 1 mg/kg, from about 0.5 µg/kg to about 500 µg/kg, from about 1 µg/kg to about 250 µg/kg, from about 1 µg/kg to about 100 µg/kg from about 1 µg/kg to about 50 µg/kg, or any range therein.

The compositions and therapies taught herein can be administered in combination. For example, the combinations can be administered, for example, for 30 minutes, 1 hour, 2 hours, 4 hours, 8 hours, 12 hours, 18 hours, 1 day, 2 days, 3 days, 4 days, 5 days, 6 days, 7 days, 8 days, 9 days, 10 days, 2 weeks, 3 weeks, 4 weeks, 6 weeks, 3 months, 6 months 1 year, any combination thereof, or any amount of time considered necessary by one of skill. The agents can be administered concomitantly, sequentially, or cyclically to a subject. Cycling therapy involves the administering a first agent for a predetermined period of time, administering a second agent or therapy for a second predetermined period of time, and repeating this cycling for any desired purpose such as, for example, to enhance the efficacy of the treatment. The agents can also be administered concurrently. The term "concurrently" is not limited to the administration of agents at exactly the same time, but rather means that the agents can be administered in a sequence and time interval such that the agents can work together to provide additional benefit. Each agent can be administered separately or together in any appropriate form using any appropriate means of administering the agent or agents.

Articles of Manufacture

The present invention provides for articles of manufacture that encompass finished, packaged and labelled pharmaceutical products. The articles of manufacture include the appropriate unit dosage form in an appropriate vessel or container such as, for example, a glass vial or other container that is hermetically sealed. In the case of dosage forms suitable for parenteral administration, the active ingredient, e.g. one or more agents including an extract taught herein, is sterile and suitable for administration as a particulate-free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In some embodiments, the unit dosage form is suitable for intravenous, intramuscular, topical or subcutaneous delivery. Thus, the invention encompasses solutions, which are preferably sterile and suitable for each route of delivery. The concentration of agents and amounts delivered are included as described herein.

As with any pharmaceutical product, the packaging material and container are designed to protect the stability of the product during storage and shipment. In addition, the articles of manufacture can include instructions for use or other information material that can advise the user such as, for example, a physician, technician or patient, regarding how to properly administer the composition as a prophylactic, therapeutic, or ameliorative treatment of the disease of concern. In some embodiments, instructions can indicate or suggest a dosing regimen that includes, but is not limited to, actual doses and monitoring procedures.

In some embodiments, the instructions can include informational material indicating that the administering of the compositions can result in adverse reactions including but not limited to allergic reactions such as, for example, anaphylaxis. The informational material can indicate that allergic reactions may exhibit only as mild pruritic rashes or may be severe and include erythroderma, vasculitis, anaphylaxis, Steven-Johnson syndrome, and the like. The informational material should indicate that anaphylaxis can be fatal and may occur when any foreign protein is introduced into the body. The informational material should indicate that these allergic reactions can manifest themselves as urticaria or a rash and develop into lethal systemic reactions and can occur soon after exposure such as, for example, within 10 minutes. The informational material can further indicate that an allergic reaction may cause a subject to experience paresthesia, hypotension, laryngeal edema, mental status changes, facial or pharyngeal angioedema, airway obstruction, bronchospasm, urticaria and pruritus, serum sickness, arthritis, allergic nephritis, glomerulonephritis, temporal arthritis, eosinophilia, or a combination thereof.

In some embodiments, the articles of manufacture can comprise one or more packaging materials such as, for example, a box, bottle, tube, vial, container, sprayer, insufflator, intravenous (I.V.) bag, envelope, and the like; and at least one unit dosage form of an agent comprising an extract taught herein within the packaging material. In some embodiments, the articles of manufacture may also include instructions for using the composition as a prophylactic, therapeutic, or ameliorative treatment for the disease of concern.

In some embodiments, the articles of manufacture can comprise one or more packaging materials such as, for example, a box, bottle, tube, vial, container, sprayer, insufflator, intravenous (I.V.) bag, envelope, and the like; and a first composition comprising at least one unit dosage form of an agent comprising an extract as taught herein within the packaging material, along with a second composition comprising a second agent such as, for example, a glycosaminoglycan, phospholipid, poly(alkylene glycol), any other bioactive agent taught herein, or any prodrugs, codrugs, metabolites, analogs, homologues, congeners, derivatives, salts and combinations thereof. In some embodiments, the articles of manufacture may also include instructions for using the composition as a diagnostic, prophylactic, therapeutic, or ameliorative treatment for the disease of concern.

Without intending to be limited to any theory or mechanism of action, the following examples are provided to further illustrate the teachings presented herein. It should be appreciated that there are several variations contemplated within the skill in the art, and that the examples are not intended to be construed as providing limitations to the claims.

Example 1

Synthesis of Rutaecarpine and Two Rutaecarpine Derivatives

Syntheses were carried out as shown in Scheme 1. Rutaecarpine (1) and two rutaecarpine derivatives containing a nitro (2) or chloro (3) group were successfully synthesized.

Scheme 1. Syntheses of rutaecarpine derivatives fropm the moiety A and B. Conditions: A) AcOH; B) heat.

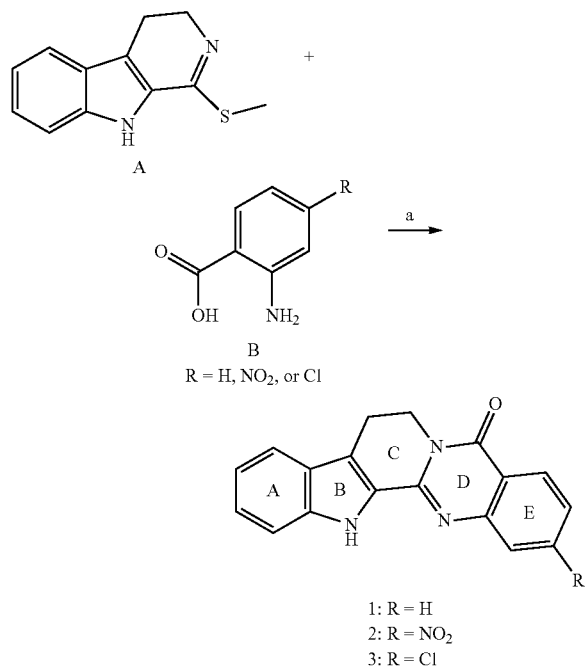

A method of synthesis of the precursor A is described in Scheme 2.

Scheme 2. Synthesis of the moiety A. Conditions: a) $CS_2$, $Et_3N$, $ClCO_2Et$; b) Concentrated $H_2SO_4$, heat; c) polyphosphoric acid, heat; d) MeI, DMF, $K_2CO_3$.

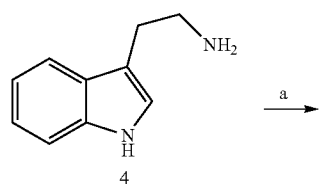

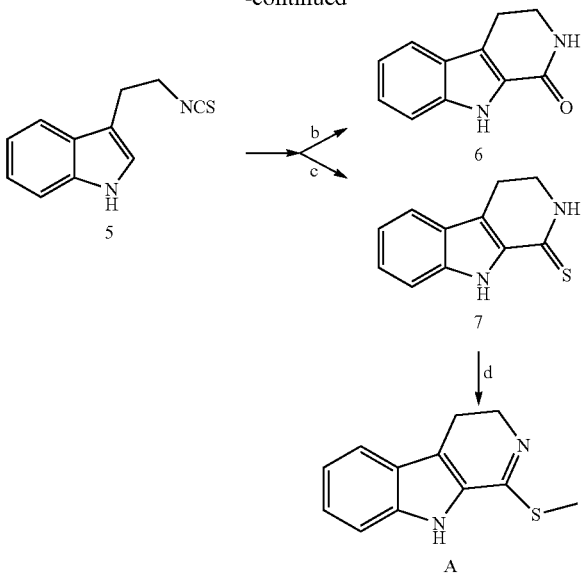

Tryptamine (4) was treated with carbon disulfide and ethyl chloroformate to yield an isocyanate (5). Acid-catalyzed cyclization of 5 using concentrated sulfuric acid yielded 6, not the target compound 7. The formation of 6 was unexpected, and initially we were not aware of it until the latter steps did not work out as planned. The structural similarity between 6 and 7 makes it difficult to distinguish these two compounds using solely $^1$H NMR. The structure of 6 was eventually determined by a combination of high resolution mass spectrometry and $^1$H and $^{13}$C NMR. The synthesis of 7 was accomplished by cyclization of 5 in the presence of polyphosphoric acid. Methylation of 7 using methyl iodide in DMF yielded compound A that is also referred to as moiety A. Rutaecarpine and its derivatives were then prepared by coupling A with commercially available aromatic amino acids, also referred to as moiety B, in acetic acid. Two electron-withdrawing groups, chloro and nitro, were selected for initial demonstration. The former is a weak electron-withdrawing group and the latter is a strong electron-withdrawing group. By tuning the electronic properties of the substituents, we can determine the substituent effect on the induction of CYP1A2. It should be appreciated that adjustment of substituent types (such as acetyl, amino, or fluorine) and their position on rings A or E can reasonably be expected to provide alternate, functional compounds.

Experiments:

Chemicals for synthesis were purchased from Fisher Scientific (Pittsburgh, Pa.) and used without further purification. Reactions were carried out under Argon using dry solvent, unless otherwise noted. $^1$H and $^{13}$C spectra were collected on a JEOL (Peabody, Mass.) ECA 600 MHz FT-NMR spectrometer. HRMS (DART-TOF) spectra were collected on a JEOL (Peabody, Mass.) Accu-TOF LC™ time-of-flight mass spectrometer equipped with an open-air ion source DART (Direct Analysis in Real Time).

Preparation of 5

In a 200 mL of round-bottomed flask, carbon disulfide (0.75 mL, 0.0124 mol) in $CH_2Cl_2$ (2 mL) was added dropwise into a $CH_2Cl_2$ solution (50 mL) of tryptamine (2 g, 0.0124 mol) and triethylamine (1.3 g, 0.0128 mol) at 0° C. After stirring at room temperature for 2 h, the reaction mixture was cooled to 0° C. Ethyl chloroformate (1.36 g, 0.0124 mol) was added dropwise into the reaction mixture and stirred for 1 h.

Et$_3$N (1.2 mL) was then added into the reaction mixture and stirred overnight at room temperature. The reaction mixture was heated to reflux for 15 min, dissolved in CH$_2$Cl$_2$ (500 mL), and washed with NaHCO$_3$ (100 mL) and H$_2$O (100 mL×2). Removal of the solvent yielded 5 (1.5 g, 60%) as a brown oil. Compound 5 was used for the next step without further purification. $^1$H NMR (CDCl$_3$) δ 8.08 (br, 1H), 7.55-7.57 (m, 1H), 7.38-7.39 (m, 1H), 7.21-7.27 (m, 1H), 7.16-7.18 (m, 1H), 7.09 (d, J=2.4 Hz, 1H), 3.76 (t, J=6.6 Hz, 2H), 3.15 (td, J=6.6, 1.2 Hz, 2H).

Preparation of 6

In a 100 mL of round-bottomed flask, concentrated H$_2$SO$_4$ was added into an acetic acid solution (20 mL) of 5 (404 mg, 2 mmol). The reaction mixture was refluxed for 2.5 h and quenched with ice water. The aqueous solution was extracted with CH$_2$Cl$_2$ (100 mL) and the organic layer was washed with brine (50 mL×2), and concentrated. Flash chromatography of the residue (silica gel, MeOH:CH$_2$Cl$_2$ 1:20) yielded 6 (160 mg, 40%) as a pale yellow solid. $^1$H NMR (CDCl$_3$) δ 10.89 (br, 1H), 7.58 (dd, J=7.8, 0.6 Hz, 1H), 7.53 (d, J=8.4 Hz, 1H), 7.23-7.29 (m, 1H), 7.08-7.15 (m, 1H), 7.05-7.08 (br, 1H), 3.70-3.73 (m, 2H), 3.02-3.08 (t, J=7.2 Hz, 2H); $^{13}$C NMR (CDCl$_3$) δ 164.1, 137.9, 126.4, 125.3, 125.2, 120.3, 120.2, 120.1, 112.9, 42.2, 20.9; HRMS (DART-TOF) calcd for C$_{11}$H$_{11}$N$_2$O (M+H$^+$) 187.0866. found 187.0874.

Preparation of 7

In a 50 mL of round-bottomed flask, 5 (504 mg, 2.5 mmol) was dissolved in polyphosphoric acid (10 g) and stirred mechanically at 100° C. for 2 h. The reaction mixture was suspended in ice water, filtered, and the obtained solid was washed with water. The yellow solid was resuspended into H$_2$O (50 mL) and extracted with CH$_2$Cl$_2$ (500 mL). Removal of the solvent yielded 7 (500 mg, 99%) as a yellow solid. $^1$H NMR (CDCl$_3$) δ 8.99 (br, 1H), 7.60-7.85 (m, 1H), 7.43 (br, 1H), 7.40-7.42 (m, 1H), 7.32-7.34 (m, 1H), 7.13-7.16 (m, 1H), 3.72-3.75 (td, J=9.0, 3.0 Hz, 2H), 3.10 (t, J=9.0 Hz, 2H); $^{13}$C NMR (CDCl$_3$) δ 185.7, 138.0, 133.5, 131.6, 125.6, 121.3, 121.2, 121.0, 113.9, 43.8, 20.5; HRMS (DART-TOF) calcd for C$_{11}$H$_{11}$N$_2$S (M+H$^+$) 203.0637. found 203.0628.

Preparation of A

In a 25 mL of round-bottomed flask, MeI (33 μL, 0.52 mmol) was added into a DMF solution (10 mL) of 7 (106 mg, 0.52 mmol) and K$_2$CO$_3$ (72 mg, 0.52 mmol). The reaction mixture was stirred overnight at room temperature and then concentrated. Flash chromatography of the residue (AcOEt: Hexane 1:1) yielded A (90 mg, 79%) as a pale yellow solid. $^1$H NMR (CDCl$_3$) δ 8.79 (br, 1H), 7.60 (d, J=7.2 Hz, 1H), 7.38-7.39 (m, 1H), 7.27-7.29 (m, 1H), 7.14-7.17 (m, 1H), 3.96 (t, 7.8 Hz, 2H), 2.90 (t, J=8.4 Hz, 2H), 2.53 (s, 3H); $^{13}$C NMR (CDCl$_3$) δ 156.8, 136.6, 128.2, 125.6, 124.8, 120.5, 120.2, 116.3, 112.2, 49.9, 19.9, 11.7; HRMS (DART-TOF) calcd for C$_{12}$H$_{13}$N$_2$S (M+H$^+$) 217.0794. found 217.0785.

General Procedure of Preparation of Rutaecarpine (1) and its Rutaecarpine Derivatives (2 and 3)

A suspension (may be solution) of A (50 mg, 0.231 mmol) and amino acids (0.231 mmol) was refluxed in acetic acid (5 mL) under Ar for 24 h. The reaction mixture was concentrated. The product was purified by either direct filtration or flash chromatography.

Compound 1, white solid, yield 44%; chromatography eluent (5% CH$_3$OH in CH$_2$Cl$_2$); $^1$H NMR (CDCl$_3$) δ 9.60 (br, 1H), 8.31-8.32 (m, 1H), 7.67-7.70 (m, 1H), 7.61-7.64 (m, 2H), 7.40-7.43 (m, 1H), 7.33-7.34 (m, 1H), 7.28-7.30 (m, 1H), 7.15-7.17 (m, 1H), 4.58 (t, J=7.2 Hz, 2H), 3.23 (t, J=7.2 Hz, 2H); $^{13}$C NMR (CDCl$_3$) δ 161.7, 147.6, 145.1, 138.4, 134.5, 127.33, 127.26, 126.7, 125.71, 125.66, 125.65, 121.3, 120.7, 120.2, 118.5, 112.2, 42.2, 19.8; HRMS (DART-TOF) calcd for C$_{18}$H$_{14}$N$_3$O (M+H$^+$) 288.1131. found 288.1121.

Compound 2, yellow solid, yield 33%; direct filtration; $^1$H NMR (DMSO-d6) δ 11.91 (br, 1H), 8.33 (d, J=9.0 Hz, 1H), 8.28 (d, J=2.4 Hz, 1H), 8.14 (dd, J=8.4, 2.4 Hz, 1H), 7.91 (s, 1H), 7.64 (d, J=7.8 Hz, 1H), 7.47 (d, J=8.4 Hz, 1H), 7.17 (t, J=7.8 Hz, 1H), 7.08 (t, J=7.8 Hz, 1H), 4.44 (t, J=6.6 Hz, 2H), 3.18 (t, J=6.6 Hz, 2H); HRMS (DART-TOF) calcd for C$_{18}$H$_{13}$N$_4$O$_3$(M+H$^+$) 333.0982. found 333.0990.

Compound 3, off white solid, yield 35%; chromatography eluent (1% CH$_3$OH in CH$_2$Cl$_2$); $^1$H NMR (DMSO-d6) δ 11.86 (br, 1H), 8.12 (d, J=8.4 Hz, 1H), 7.63 (d, J=7.8 Hz, 1H), 7.61 (d, J=1.8 Hz, 1H), 7.45-7.48 (m, 2H), 7.24-7.26 (m, 1H), 7.06-7.08 (m, 1H), 4.40 (t, J=6.6 Hz, 2H), 3.16 (t, J=7.2 Hz, 2H); HRMS (DART-TOF) calcd for C$_{18}$H$_{13}$ClN$_3$O (M+H$^+$) 322.0742. found 322.0746.

One of skill will appreciated that there are a variety of chemical analytical techniques available to obtain qualitative and quantitative measures for the experiments taught herein. Any technique known to one of skill can be used to obtain the desired data.

Liquid Chromatography

HPLC is performed with an equivalent chromatographic pump, injector equipped with a sampling loop and ultraviolet detector. Separation is achieved by a comparable reversed-phase C18 column. The mobile phase has acetonitrile-0.1 M KH2P04 (15:85, v/v) at flow rate of 1 mL/min, and wavelength of 270 nm. Output data from the detector is integrated using an EZChrom chromatographic data system or equivalent. Validation is for both intra- and inter-day accuracy (−0.1-8.0%) and precision (0.1-12%). Under the experimental conditions described above, the targets for limit of detection are approx. 0.01 ug/mL, and signal-to-noise ratio of 3:1. The lower limit of quantification is targeted at the lowest concentration of analyte, 0.05 ug/mL.

LC-Tandem Mass Spectrometry

LC-MS-MS analysis may be performed in place of regular HPLC using a Waters 2690 with 996 photodiode assay (PDA) detector, or equivalent, with an automatic liquid chromatographic sampler, or equivalent, and an autoinjection system hyphenated to a Micromass Quattro Ultima tandem quadrupole mass spectrometry equipped with an electrospray ionization (ESI) source or equivalent. The separation can then be achieved using a Phenomenex reversed-phase Luna C12 column or comparable. The solvent delivery system is kept constant at 0.8 mL/min and the mobile phase will consist of 80% methanol. The volume of the injection is 10 uL. For operation in the MS-MS mode, a mass spectrometer with an orthogonal Z-spray ESI is used. The infusion experiment is performed using a Mode 22 multiple syringe pump, or equivalent. During the analyses, the ESI parameters is set as follows: capillary voltage, 3.0 kV for positive mode; source temperature, 80 C; desolvation temperature, 300 C; cone gas flow, 95 L/h; and desolvation gas flow, 440 L/h. The cone voltage of m/z=288 is 70 V and the collision voltages are 30 eV. All LC-MS-MS data is processed by the MassLynx version 4.0 NT Quattro data acquisition software or equivalent.

Example 2

MEROD Assay of Rutaecarpine and Two Synthesized Rutaecarpine Derivatives

Any technique known to one of skill can be used to determine the functionality and activity of the teachings provided herein. The present example illustrates a MEROD assay.

FIG. 1 illustrates how caffeine is primarily metabolized to paraxanthine via CYP1A2 enzyme in a human, according to some embodiments. The MEROD (methoxyresorufin-O-demethylase) assay measures the activity of the enzyme (CYP1A2) that converts methoxyresorufin (probe substrate) to resorufin (demethylation) in the presence of NADPH. The resulting resorufin concentration can be measured using a fluorescence reader by setting the excitation and emission wavelengths at 544 and 590 nm, respectively.

To test whether rutaecarpine and two rutaecarpine derivatives (chloro-rutaecarpine and nitro-rutaecarpine) can induce CYP1A2 enzyme, Hepa1c1c7 cells (mouse hepatoma) were incubated with rutaecarpine, rutaecarpine derivatives, 3-MC (positive control) or DMSO (negative control) and MEROD assay was performed on live cells or the isolated microsomes.

Experiments

Preparation of Microsomes from Cells Incubated with Rutaecarpine, Chloro-Rutaecarpine and Nitro-Rutaecarpine.

Hepa1c1c7 cells were grown in DMEM supplemented with 10% FBS, 1% glutaMAX-1, 10 U/ml of penicillin, and 10 μg/ml of streptomycin in 150-mm dishes. When cells were ~90% confluent, 30 μL of 1 mM rutaecarpine, nitro-rutaecarpine, chloro-rutaecarpine, 3-methylcholanthrene (3-MC, as the positive control for CYP1A2 induction) or DMSO was added to cells in the presence of 15 mL growth media. After approximately 22 hours of incubation, cells were washed with ice-cold phosphate-buffered saline (PBS), scraped into 15-mL Falcon tubes and pelleted down by centrifuging at ~600 g for 5 minutes at room temperature (RT). The pellets were stored at −80° C. until further processing. Each of the stored pellets was resuspended in ~7.5 mL sample lysis buffer (1 mM PMSF, 2 mg/L leupeptin in 0.1 M phosphate buffer pH 7.4). Resuspended cells were sonicated on ice at setting 5 for 15 seconds and repeated once. The suspensions were centrifuged at 10,000 g for 20 minutes at 4° C. and the resulting supernatants were centrifuged further at 100,000 g for 1 hour at 4° C. The resulting pellets were resuspended with 200 μL 0.1 M phosphate buffer pH 7.4 and ~50 μL was aliquoted/Eppendorf tube and stored at −80° C. To determine the protein concentration of the microsomes, BCA (bicinchoninic acid) assay was performed using the kit from Thermo Scientific.

MEROD Assay

MEROD assays were performed using live Hepa1c1c7 cells preincubated with either 2 μM rutaecarpine, nitro-rutaecarpine, chloro-rutaecarpine, or DMSO, as well as microsomes generated from Hepa1c1c7 cells incubated with either 2 μM rutaecarpine, nitro-rutaecarpine, chloro-rutaecarpine, 3-MC or DMSO.

For the microsome study, the metabolism of methoxyresorufin was performed as follows: the final incubation mixture (100 μL total) contained 1 mg/mL microsomal protein, 5 mM methoxyresorufin and 5 mM NADPH (or no NADPH for the control study) in 0.1 M phosphate buffer pH 7.4. The reaction mixture (minus the NADPH) was preincubated at 37° C. for approximately 5 minutes and then the reaction was started by the addition of either NADPH solution (or phosphate buffer for the control study). After 60-minute incubation at 37° C., 50 μL aliquot was taken and the reaction was stopped by addition of an equal volume of acetonitrile. The mixture was vortex and centrifuged at RT at 12,000 g for approximately 5 minutes. The resulting supernatants were placed into the wells of a 96-well fluorescence plate. Similar procedures were performed for the remaining reaction mixtures after an 85-minute incubation at 37° C. The concentration of resorufin was measured by setting the excitation and emission wavelengths at 544 and 590 nm, respectively.

For MEROD assay in live cells, Hepa1c1c7 cells were cultured in either 6-well or 24-well-plates. For the 24-well plate experiment, after confluent cells were incubated for approximately 20 hours with either resorufin, nitro-resorufin, chloro-resorufin, 3-MC or DMSO (in triplicates), culture media was removed and 180 μL fresh culture media containing 5 mM methoxyresorufin was added per well. After 1 hour incubation at 37° C., 100 μL aliquot was taken from each well and the formation of resorufin was measured by fluorescence. For the 6-well plate experiment, after trypsinized cells were incubated for approximately 24 hours with either resorufin, nitro-resorufin, chloro-resorufin, or DMSO (in triplicates), culture media was removed and 1000 μL fresh culture media containing 5 mM methoxyresorufin was added per well. After 5 hours incubation at 37° C., 100 μL aliquot was taken from each well, centrifuged at 12,000 g at RT for ~5 min and the supernatants were placed into wells of a 96-well fluorescence plate and the formation of resorufin was measured by fluorescence.

Microsome Experiment

Data from MEROD assays show a significant difference in the formation of resorufin from microsomes that were generated from cells. The cells were incubated with 2 μM rutaecarpine and chloro-rutaecarpine compared to cells incubated with 3-MC, the positive control.

Figure 2:
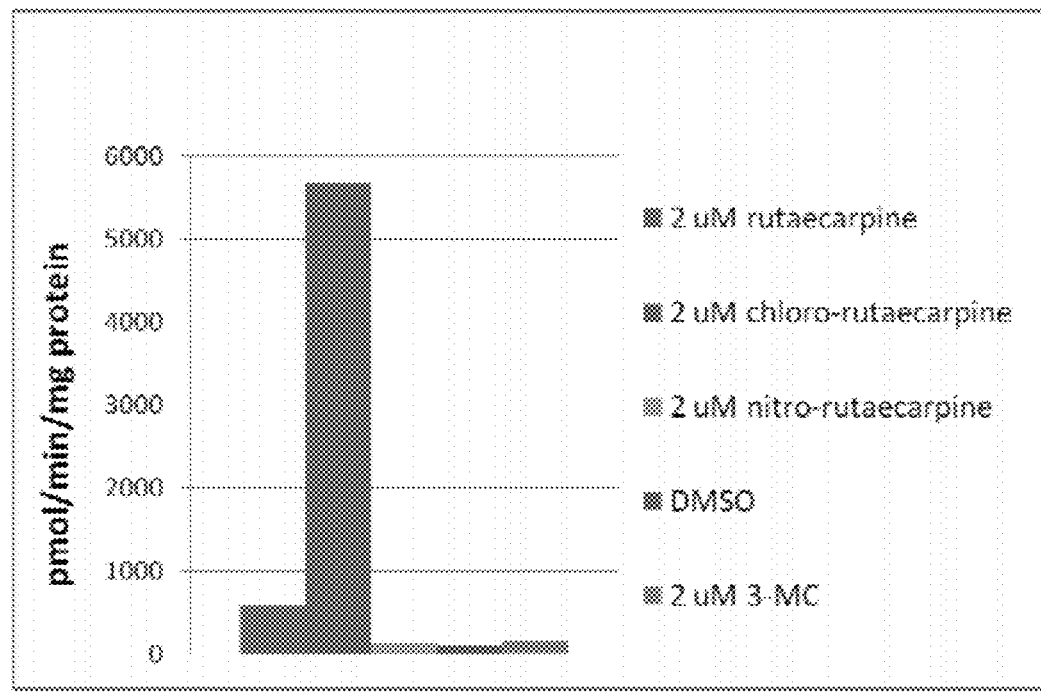
FIG. 2 shows MEROD assay data (60-minute time-point) from microsomes generated from cells incubated with 2 μM rutaicarpine, nitro-rutaecarpine, chloro-rutaecarpine, 3-MC or DMSO, according to some embodiments.
Figure 3:
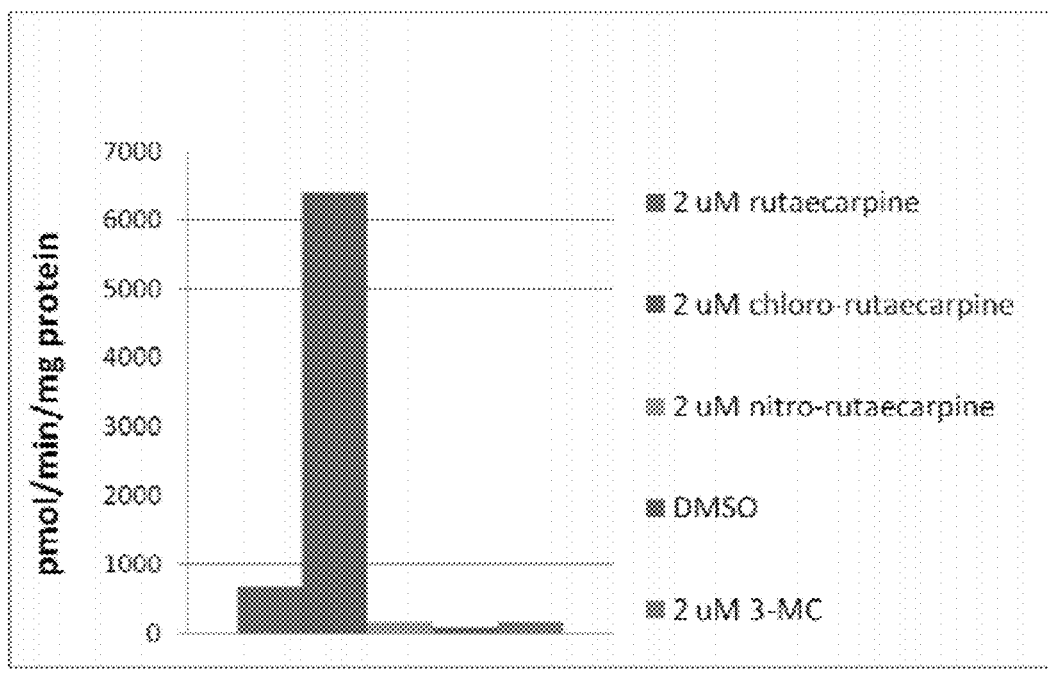
FIG. 3 shows MEROD assay data (85-minute time-point) from microsomes generated from cells incubated with 2 μM rutaicarpine, nitro-rutaecarpine, chloro-rutaecarpine, 3-MC or DMSO, according to some embodiments.

FIG. 2 shows MEROD assay data (60-minute time-point) from microsomes generated from cells incubated with 2 μM rutaicarpine, nitro-rutaecarpine, chloro-rutaecarpine, 3-MC or DMSO, according to some embodiments. FIG. 3 shows MEROD assay data (85-minute time-point) from microsomes generated from cells incubated with 2 μM rutaicarpine, nitro-rutaecarpine, chloro-rutaecarpine, 3-MC or DMSO, according to some embodiments. As shown by FIGS. 2 and 3, the formation of resorufin from microsomes generated from cells incubated with 2 μM nitro-rutaecarpine was comparable to that of 3-MC and not very different from the negative control (DMSO).

Assay in Live Cells

MEROD assay in live cells also show significant difference in the formation of resorufin from cells incubated with 2 μM chloro-rutaecarpine compared to DMSO.

Figure 4:
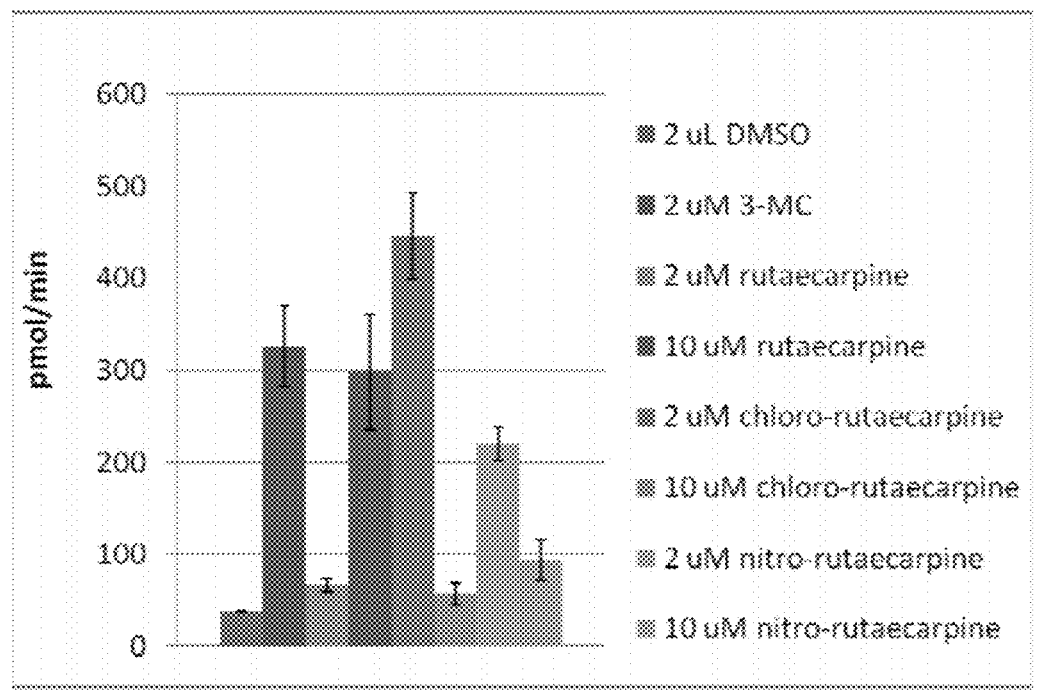
FIG. 4 shows MEROD assay data from cells incubated with 2 μM rutaecarpine, nitro-rutaecarpine, chloro-rutaecarpine or DMSO (24-well plate study), according to some embodiments.
Figure 5:
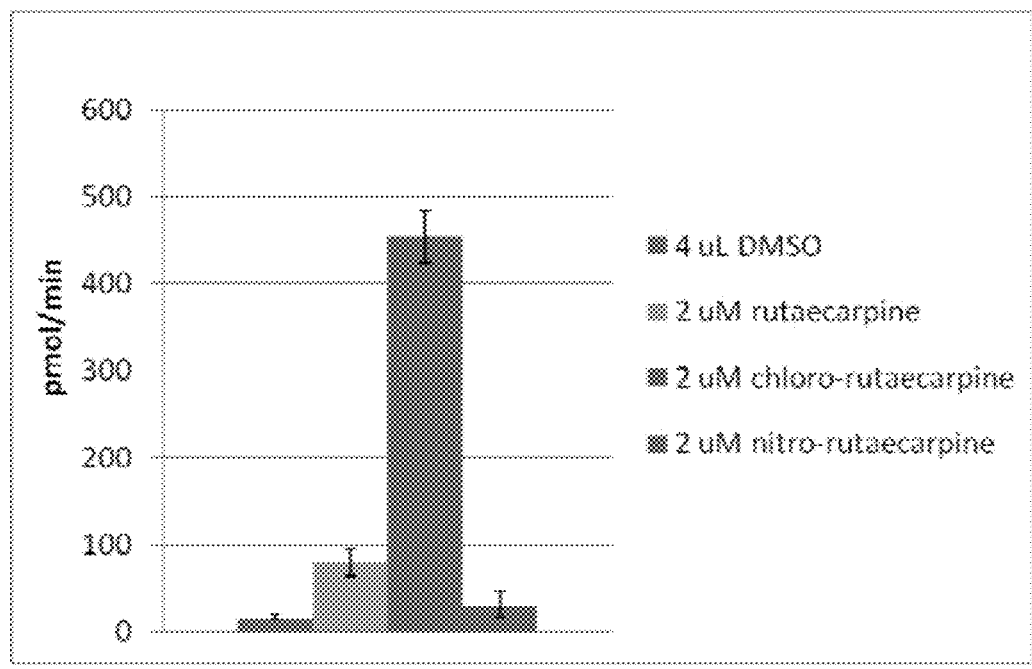
FIG. 5 shows MEROD assay data from cells incubated with 2 μM rutaecarpine, nitro-rutaecarpine, chloro-rutaecarpine or DMSO (6-well plate study), according to some embodiments.

FIG. 4 shows MEROD assay data from cells incubated with 2 μM rutaecarpine, nitro-rutaecarpine, chloro-rutaecarpine or DMSO (24-well plate study), according to some embodiments. FIG. 5 shows MEROD assay data from cells incubated with 2 μM rutaecarpine, nitro-rutaecarpine, chloro-rutaecarpine or DMSO (6-well plate study), according to some embodiments.

It should be appreciated that there is no marked difference in cells incubated with 10 μM chloro-rutaecarpine. This could be due, perhaps, to cell death associated with higher concentration of chloro-rutaecarpine. A BCA assay can be performed to determine the total protein concentration of the cells from each well of the 24-well plate that was used for the MEROD assay (currently stored at −80° C.). Surprisingly, however, we found that our rutaecarpine derivatives showed at least a 7-fold increase in potency over rutaecarpine, in some embodiments.

Example 3

Animal Testing of Rutaecarpine Derivatives

Any technique known to one of skill can be used to determine the functionality and activity of the compounds, compositions, and formulations in the teachings provided herein. The teachings of Tsai, et al., for example, can be used as a testing method. See, Tsai, et al. Planta Med. 75(7):640-5 (2005), which is hereby incorporated by reference herein in its entirety.

Animals

Male, specific pathogen-free rats will be obtained by a Laboratory Animal Center. The animals will have free access to food and water until 18 h prior to being supplied for the experiments, at which time only food will be removed. The rats will initially be anesthetized with urethane 1 g/mL or equivalent and a-chloralose 0.1 g/mL or equivalent, and will remain anesthetized throughout the experimental period. The femoral vein will be exposed for further drug administration. The rat body temperature will be maintained at 37 C with a heating pad during the experiment. All experimental protocols involving animals will be approved by the appropriate committees as required by the FDA.

Drug Administration

The drug will be administered in doses yet to be determined. Each rutaecarpine derivative will be dissolved in corn oil for administration. Each test group will be treated by gastro gavage consecutively for 3 days. On the fourth day, the rats will be administered caffeine at 5 mg/kg via the femoral vein. The rats in the control group will receive the same amount of corn oil orally for 3 consecutive days and on the fourth day caffeine at 5 mg/kg will be injected via the femoral vein. Plasma levels of caffeine will be measured by HPLC or LCMS.

Pharmacokinetics and Statistical Analysis

Pharmacokinetic calculations will then be performed on each individual animal's data using pharmacokinetic calculation software equivalent to WinNonlin Standard Edition Version 1.1 by a non-compartmental method. Statistical analysis will be performed with SPSS version 10.0 or equivalent. The comparison between the control group, and rutaecarpine's derivatives will be calculated via a One-way ANOVA. Statistical tests will be performed at two-sided 5% level of significance.

It should be appreciated that the experimental conditions provided herein are for illustration and example only. One of skill can vary the experimental conditions to suit a particular or alternate experimental design. The experimental conditions can be in vitro or in vivo, or designed for any subject, for example, human or non-human. For example the liquid chromatography and mass spectroscopy conditions and specifications can be varied depending on the experimental methods chosen. Moreover, the animal testing in general can be varied to suit a desired experimental method. For example, it should be appreciated that, generally speaking, plasma samples can be taken at pre-determined time points and caffeine concentration can be measured with a validated method, such as HPLC or an LC-MS/MS method, although other methods are possible. And, caffeine PK parameters can be calculated with a non-compartmental method, or any other method, depending on the choice of experimental design.

We claim:

1. A compound of the following structure:

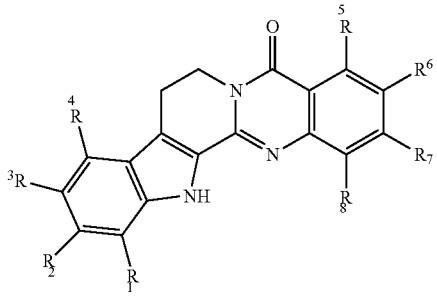

or salts, hydrates or solvates thereof; wherein,
at least one of $R_1$-$R_5$ or $R_8$ is an independently selected electron withdrawing group;
$R_6$ is an independently selected electron withdrawing group selected from the group consisting of F, I, nitro, acyl, formyl, an alkylsulfonyl having from 1 to 4 carbon atoms, an arylsulfonyl having from 6 to 15 carbon atoms, a fluoromethyl, and cyano group;
$R_7$ is an independently selected electron withdrawing group selected from the group consisting of F, Br, I, nitro, acyl, formyl, an alkylsulfonyl having from 1 to 4 carbon atoms, an arylsulfonyl having from 6 to 15 carbon atoms, a fluoromethyl, and cyano group; and,
the remainder of $R_1$-$R_7$ or $R_8$ is hydrogen, a $(C_1$-$C_4)$ alkyl group, or a substituted $(C_1$-$C_4)$ alkyl group.

2. A pharmaceutical formulation comprising the compound of claim 1 and a pharmaceutically acceptable excipient.

3. The compound of claim 1, wherein
at least one of $R_1$-$R_5$ or $R_8$ is an independently selected electron withdrawing group selected from the group consisting of a $NO_2$, a halogen, or an acetyl group;
$R_6$ is an independently selected electron withdrawing group selected from the group consisting of a $NO_2$, F, I, and an acetyl group;
$R_7$ is an independently selected electron withdrawing group selected from the group consisting of a $NO_2$, F, Br, I, and an acetyl group; and,
the remainder of $R_1$-$R_7$, or $R_8$ is hydrogen, a $(C_1$-$C_4)$ alkyl group, or a substituted $(C_1$-$C_4)$ alkyl group.

4. The compound of claim 1 consisting of

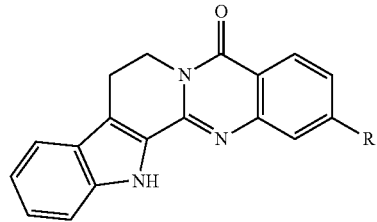

or salts, hydrates or solvates thereof; wherein,
R is $NO_2$, F, Br, I, or an acetyl group.

5. A pharmaceutical formulation comprising the compound of claim 4 and a pharmaceutically acceptable excipient.

6. The compound of claim 4, wherein R is F.

7. The compound of claim 1 consisting of the formula:

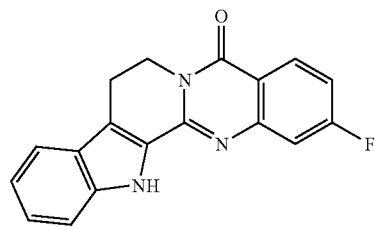 [SMILES: O=c1c2ccc(F)cc2nc2n1CCc1c-2[nH]c2ccccc12]

or salts, hydrates or solvates thereof.

8. An article of manufacture comprising (i) the compound of claim 1 and (ii) instructions for administering an effective amount of the compound to a subject to increase the activity of CYP1A2 in the subject.

9. An article of manufacture comprising (i) the compound of claim 4 and (ii) instructions for administering an effective amount of the compound to a subject to increase the activity of CYP1A2 in the subject.

10. An article of manufacture comprising (i) the compound of claim 7 and (ii) instructions for administering an effective amount of the compound to a subject to increase the activity of CYP1A2 in the subject.

11. A method of increasing the activity of CYP1A2 in a subject, comprising administering an effective amount of the following compound to the subject:

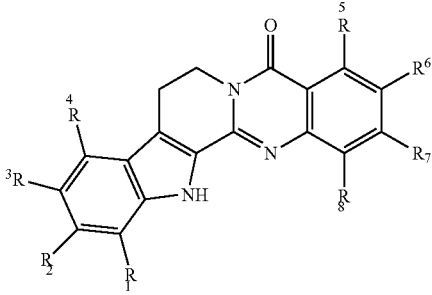

or salts, hydrates or solvates thereof; wherein,
at least one of $R_1$-$R_7$ or $R_8$ is an independently selected electron withdrawing group; and,
the remainder of $R_1$-$R_7$ or $R_8$ is hydrogen, a ($C_1$-$C_4$) alkyl group, or a substituted ($C_1$-$C_4$) alkyl group;
wherein the administering increases the activity of CYP1A2 in the subject when compared to a control group that does not receive the compound.

12. The method of claim 11, wherein the compound has the following structure:

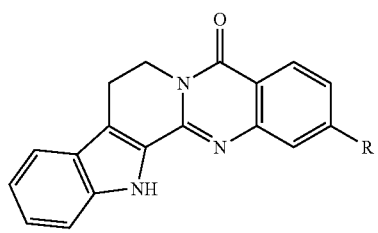

or salts, hydrates or solvates thereof; wherein,
R is $NO_2$, a halogen, or an acetyl group;
wherein, the administering increases the activity of CYP1A2 in the subject when compared to a control group that does not receive the compound.

13. The method of claim 11, wherein the compound has the following structure:

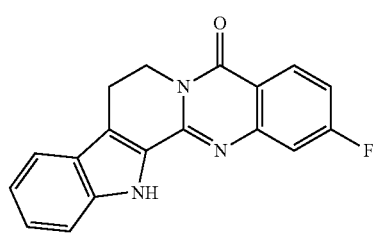

or salts, hydrates or solvates thereof;
wherein the administering increases the activity of CYP1A2 in the subject when compared to a control group that does not receive the compound.

14. A method of treating symptoms of caffeine withdrawal in a subject, comprising administering to the subject a combination of (i) an effective amount of the following compound:

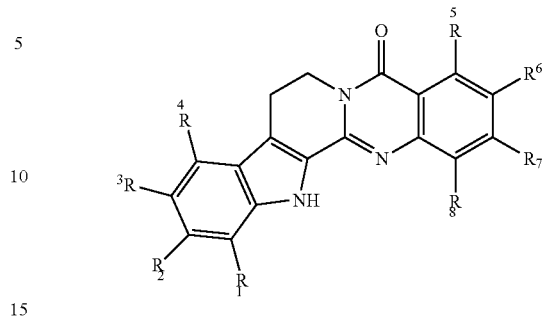

or salts, hydrates or solvates thereof; wherein,
at least one of $R_1$-$R_7$ or $R_8$ is an independently selected electron withdrawing group; and,
the remainder of $R_1$-$R_7$ or $R_8$ is hydrogen, a ($C_1$-$C_4$) alkyl group, or a substituted ($C_1$-$C_4$) alkyl group;
and in combination with (ii) an analgesic;
wherein, the administering reduces the caffeine level in the subject, and ameliorates the symptoms experienced by the subject, when compared to a control group that does not receive the compound.

15. The method of claim 14, further comprising administering an effective amount of caffeine to the subject.

16. A method of treating theophylline toxicity in a subject, comprising administering an effective amount of the following compound to the subject:

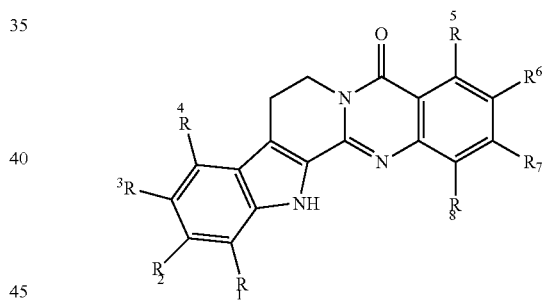

or salts, hydrates or solvates thereof; wherein,
at least one of $R_1$-$R_7$ or $R_8$ is an independently selected electron withdrawing group; and,
the remainder of $R_1$-$R_7$ or $R_8$ is hydrogen, a ($C_1$-$C_4$) alkyl group, or a substituted ($C_1$-$C_4$) alkyl group;
wherein the administering reduces the theophylline level in the subject when compared to a control group that does not receive the compound of claim 1.

17. The method of claim 16, further comprising administering an effective amount of theophylline to the subject.

18. The method of claim 16, further comprising administering an effective amount of an analgesic to the subject.

19. The method of claim 16, further comprising administering a combination of an effective amount of theophylline and an effective amount of an analgesic to the subject.

20. A method of treating a cardiovascular disorder in a subject that has consumed caffeine, comprising administering an effective amount of the following compound to the subject:

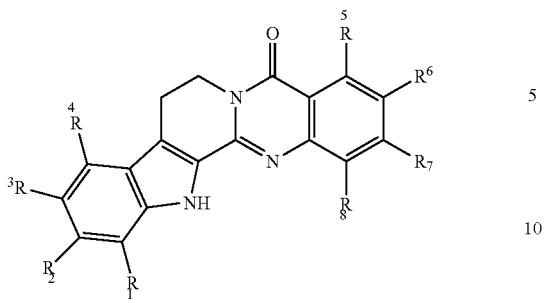

or salts, hydrates or solvates thereof; wherein,
at least one of $R_1$-$R_7$ or $R_8$ is an independently selected electron withdrawing group; and,
the remainder of $R_1$-$R_7$ or $R_8$ is hydrogen, a ($C_1$-$C_4$) alkyl group, or a substituted ($C_1$-$C_4$) alkyl group;
wherein the administering reduces the caffeine level in the subject, and ameliorates symptoms of the cardiovascular disorder in the subject, when compared to a control group that does not receive the compound.

* * * * *